United States Patent
Kilambi

(10) Patent No.: US 8,119,823 B2
(45) Date of Patent: Feb. 21, 2012

(54) SOLVO-THERMAL HYDROLYSIS OF XYLOSE

(75) Inventor: Srinivas Kilambi, Marietta, GA (US)

(73) Assignee: Renmatix, Inc., Kennesaw, GA (US)

( * ) Notice: Subject to any disclaimer, the term of this patent is extended or adjusted under 35 U.S.C. 154(b) by 236 days.

(21) Appl. No.: 12/504,628

(22) Filed: Jul. 16, 2009

(65) Prior Publication Data

US 2010/0048924 A1     Feb. 25, 2010

Related U.S. Application Data

(60) Provisional application No. 61/081,337, filed on Jul. 16, 2008, provisional application No. 61/081,346, filed on Jul. 16, 2008, provisional application No. 61/081,348, filed on Jul. 16, 2008, provisional application No. 61/092,680, filed on Aug. 28, 2008, provisional application No. 61/224,809, filed on Jul. 10, 2009.

(51) Int. Cl.
  *C07D 307/48*  (2006.01)
  *B01J 19/00*   (2006.01)
(52) U.S. Cl. ........................... 549/489; 422/198
(58) Field of Classification Search .................. 549/489; 422/198
  See application file for complete search history.

(56) References Cited

U.S. PATENT DOCUMENTS

| | | | |
|---|---|---|---|
| 4,308,200 | A  | 12/1981 | Fremont |
| 4,338,199 | A  | 7/1982  | Modell |
| 4,366,322 | A  | 12/1982 | Raymond |
| 4,493,797 | A  | 1/1985  | Avedesian |
| 4,543,190 | A  | 9/1985  | Modell |
| 4,675,198 | A  | 6/1987  | Sevenants |
| 5,009,746 | A  | 4/1991  | Hossain et al. |
| 5,328,934 | A  | 7/1994  | Schiraldi |
| 5,512,231 | A  | 4/1996  | Thies et al. |
| 5,516,952 | A  | 5/1996  | Lee et al. |
| 5,788,812 | A  | 8/1998  | Agar et al. |
| 5,830,763 | A  | 11/1998 | Junk et al. |
| 6,180,845 | B1 | 1/2001  | Catallo et al. |
| 6,642,396 | B1 | 11/2003 | Zeitsch et al. |
| 6,743,928 | B1 | 6/2004  | Zeitsch |
| 6,921,820 | B2 | 7/2005  | Arai et al. |
| 7,666,637 | B2 | 2/2010  | Nguyen |
| 2007/0161095 | A1 | 7/2007 | Gurin |
| 2007/0267008 | A1 | 11/2007 | Funazukuri et al. |
| 2008/0015336 | A1 | 1/2008 | Cornish et al. |
| 2009/0056201 | A1 | 3/2009 | Morgan |
| 2009/0288788 | A1 | 11/2009 | Castor |
| 2010/0043782 | A1 | 2/2010 | Kilambi |
| 2010/0048884 | A1 | 2/2010 | Kilambi |
| 2010/0069626 | A1 | 3/2010 | Kilambi |

FOREIGN PATENT DOCUMENTS

| | | |
|---|---|---|
| DE | 10259928 A1    | 7/2004 |
| JP | 2005296906     | 10/2005 |
| WO | WO-2007056701  | 5/2007 |
| WO | WO-2009015409  | 2/2009 |
| WO | WO-2010009343  | 1/2010 |
| WO | WO-2011091044  | 7/2011 |

OTHER PUBLICATIONS

Holgate et al. AIChE Journal, 1995, 41(3), 637-6.*
Lu et al. STN Accession No. 2008:1016799, Document No. 151:427986. Abstract of Transactions of Tranjin University, 2008, 14(3), 198-201.*
Siato et al. Journal of Physics:Cinference Series, 2008, 121.*
Wiboonsiriku et al. Journal of Agricultural and Food Chemistry, 2007, 55(21), 8759-8765.*
Moreschi et al. Journal of Agricultural and Food Chemistry, 2004, 52(6), 1753-1758.*
PCT Application No. PCT/US2009/050898, International Preliminary Report on Patentability mailed Jan. 18, 2011.
PCT Application No. PCT/US2009/050898, International Search Report and Written Opinion mailed Feb. 8, 2010.
"Supercritical Fluids", Kirk-Othmer Encyclopedia of Chemical Technology 3rd ed., John Wiley & Sons, New York, 1978.
Adschiri, et al., "Noncatalytic Conversion of Cellulose in Supercritical and Sub-Critical Water", Journal of Chemical Engineering of Japan, 1993, 26(6):676-680.
Bennett, et al., "Chemicals from Forest Products by Supercritical Fluid Extraction", Fluid Phase Equil., 1983, 10:337.
Bicker, et al., "Catalytical conversion of carbohydrates in subcritical water: A new chemical process for lactic acid production", Journal of Molecular Catalysis A: Chemical 239, 2005, 151-157.
Boocock, et al., "Liquefaction of Biomass by Rapid Hydrolysis", Can. J. Chem. Eng., 1983, 61:80.
Chamblee, et al., "Reversible in situ acid formation for β-pinene hydrolysis using $CO_2$ expanded liquid and hot water", Green Chemistry, 2004, vol. 6, 382-386.

(Continued)

*Primary Examiner* — Nizal Chandrakumar
(74) *Attorney, Agent, or Firm* — Kilpatrick Townsend & Stockton LLP

(57) ABSTRACT

The invention relates to a process for producing furfural from xylose comprising: (a) mixing an aqueous xylose solution containing xylose oligosaccharides with sub-critical or near-critical water to form a mixture at a first temperature and a first pressure; (b) maintaining the mixture at the first temperature and the first pressure for a first time period; and (c) rapidly cooling the mixture to a second temperature and a second pressure, wherein furfural is produced by the process (d) process can also be carried out with or without mixing of carbon dioxide with aqueous xylose solution before it is mixed with sub-critical or near-critical water to form a mixture at a first temperature and pressure.

13 Claims, 10 Drawing Sheets

OTHER PUBLICATIONS

Dias, et al. "Dehydration of xylose into fufural over micro-mesoporous sulfonic acid catalysts", Journal of Catalysis 229, 2005, 414-423.

Eckert, et al., "Environmental Science and Technology", 1986, 20:319-325.

Ehara, et al. "A comparative study on chemical conversion of cellulose between the batch-type and flow-type in supercritical water", Cellulose, 2002, 9:301-311.

Ehara, et al. "Chemical conversion of woody biomass by supercritical water-Degradation of lignin-", Graduate School of Energy Science, Kyoto University, Kyoto Japan, Jun. 2002.

Erzengin, et al., "Liquefaction of Sunflower Stalk by Using Supercritical Extraction", Energy Conversion and Management, Elsevier Science Publishers, Oxford, GB Aug. 1998, 39:11, 1203-1206.

Guirong, et al., "Cellulose decomposition behavior in hot-compressed aprotic solvents", Science in China Series B: Chemistry, May 2008, vol. 51, No. 5, 479-486.

Houghton, et al., "Reactivity of Some Organic Compounds with Supercritical Water", Fuel 1986, 61:827.

Kim, et al., "Selective Synthesis of Furfural from Xylose with Supercritical Carbon Dioxide and Solid Acid Catalyst", Journal of Industrial and Engineering Chemistry, The Korean Society of Industrial and Engineering Chemistry, Korea 2001, 7(6); 424-429.

Knopf, et al., "Reactive Extraction of Lignin from Biomass Using Supercritical Ammonia-Water Mixtures", J. Supercritical Fluids 1993, 6:249-254.

Li, et al., "Interaction of Supercritical Fluids with Lignocellulosic Materials", Industrial and Engineering Chemistry Research 1988, 27(7): 1301-1312.

Marchessault, et al., "A New Understanding of the Carbohydrate System", Future Sources of Organic Raw Materials 1980, 613-625.

Matsumura, et al. "Supercritical Water Treatment of Biomass for Energy and Material Recovery", Combust. Sci. and Tech., 2006, 178: 509-536.

McCoy, et al., "Extraction of Lignin from Biomass with Supercritical Alcohol", J. Supercritical Fluids 1989, 2:80-84.

McHugh, et al., "Supercritical Fluid Extraction : Principles and Practice", Butterworths 1986, 309-310.

Miyazawa, et al., "Polysaccharide Hydrolysis Accelerated by Adding Carbon Dioxide under Hydrothermal Conditions", Biotechnol. Prog. 2005, 21:1782-1785.

Modell, et al., "Supercritical Water Oxidation of Pulp Mill Sludges", TAPPI J. 1992, 75:195.

Ogihara, et al. "Direct observation of cellulose dissolution in subcritical and supercritical water over a wide range of water densities (500-1000 kg/m$^3$)", Cellulose, 2005, 12:595-606.

Osada, et al., "Low Temperature Catalytic Gasification of Lignin and Cellulose with a Ruthenium Catalyst in Supercritical Water", Energy Fuels 2004, 18: 327-333.

Pasquini, et al., "Extraction of Lignin from sugar cane bagasse and *Pinus taeda* wood chips using ethanol-water mixtures and carbon dioxide at high pressures", Journal of Supercritical Fluids, PRA Press, US Nov. 2005, 36(1); 31-39.

Persson, et al., "Supercritical Fluid Extraction of a Lignocellulosic Hydrolysate of Spruce for Detoxification and to Facilitate Analysis of Inhibitors", Biotechnology and Bioengineering, Wiley & Sons , Hoboken, NJ, US Sep. 20, 2002, 79(6):694-700.

Peter, et al., "High Pressure Extraction of Lignin from Biomass", Supercritical Fluid Technology, p. 385 (1985).

Rao, et al., "Pyrolysis Rates of Biomass Materials", Energy 1998, 23:973-978.

Sako, "Kinetic study of furfural formation accompanying supercritical carbon dioxide extraction", Journal of Chemical Engineering of Japan, Society of Chemical Engineers Aug. 1, 1992, 25(4):372-377.

Sangarunlert, et al., "Furfural production by acid hydrolysis and supercritical carbon dioxide extraction from rice husk", Korean Journal of Chemical Engineering 2007, 24(6): 936-941.

Sasaki, et al., "Cellulose Hydrolysis in Sub-Critical and Supercritical Water", Journal of Supercritical Fluids 1998, 13:261-268.

Sina, et al. "Key Compounds of the Hydropyrolysis of Glucose in Supercritical Water in the Presence of $K_2CO_3$", Ind. Eng. Chem. Res., 2003, 42(15), 3516-3521.

Walsum, et al. "Carbonic acid enhancement of hydrolysis in aqueous pretreatment of corn stover", Bioresource Technology 93, 2004, 271-226.

Yoshida, et al., "Gasification of Biomass Model Compound and Real Biomass in Supercritical Water", Biomass and Bioenergy, 26:71-78 (2004).

International PCT Application No. PCT/US2011/21726, International Search Report and Written Opinion dated Jul. 5, 2011.

Li et al., "Interaction of Supercritical Fluids with Lignocellulosic Materials", Industrial Engineering Chemistry Research, American Chemical Society Res., Jul. 1988, 27(7):1301-1312.

Zhao, et al., "Supercritical hydrolysis of cellulose for oligosaccharide production in combined technology", Chemical Engineering Journal, Aug. 1, 2009, 150(2):411-417.

Pasquini, Daniel et al., "Sugar cane bagasse pulping using supercritical $CO^2$ associated with co-solvent 1-butanol/water", J. of Supercritical Fluids, vol. 34; pp. 125-134 (2005).

Schacht, Christian et al., "From plant materials to ethanol by means of supercritical fluid technology", J. of Supercritical Fluids, vol. 46; pp. 299-321 (2008).

U.S. Appl. No. 12/504,636, Office Action mailed Nov. 10, 2011 (22 pages).

* cited by examiner

US 8,119,823 B2

SOLVO-THERMAL HYDROLYSIS OF XYLOSE

CROSS-REFERENCE TO RELATED APPLICATIONS

This application claims priority to U.S. Provisional Patent Application No. 61/081,337 filed Jul. 16, 2008, U.S. Provisional Patent Application No. 61/081,346 filed Jul. 16, 2008, U.S. Provisional Patent Application No. 61/081,348 filed Jul. 16, 2008, U.S. Provisional Patent Application No. 61/092,680 filed Aug. 28, 2008, and U.S. Provisional Patent Application No. 61/224,809 filed Jul. 10, 2009, the disclosures of each of which are incorporated herein by reference in their entireties. This application is related to and incorporates by reference the following PCT application filed on even date herewith: "NANO-CATALYTIC-SOLVO-THERMAL TECHNOLOGY PLATFORM BIO-REFINERIES", inventors Srinivas Kilambi and Kiran L. Kadam.

STATEMENT OF RIGHTS TO INVENTIONS MADE UNDER FEDERALLY SPONSORED RESEARCH

Not applicable.

BACKGROUND OF THE INVENTION

Xylose is a compound that is used in pharmaceuticals, diagnostics, sugar substitutes for diabetics, and as an intermediate in making furfural. Furfural has been made by a variety of methods.

"Quaker Oats" used cereal processing reactors for the first industrial production of furfural. Later on, Rosenlew and Wyss were able to produce furfural from wood pulp processing reactors. These reactors are able to produce furfural but with very low productivity.

Since then many inventors have tried to increase the productivity of furfural by using mineral acids and other costly reactants. For examples, U.S. Pat. No. 6,743,928 describes the process of manufacturing furfural using acidic conditions; U.S. Pat. No. 6,642,396 describes the production of furfural from lignosulphonate waste liquor; U.S. Pat. No. 5,788,812 describes the method of recovering furfural from organic pulping liquor; and U.S. Pat. No. 4,366,322 describes the method of production of furfural from vegetable matter.

Production of furfural has great importance because of its industrial utility. However, there have been many problems reported for the production of furfurals from xylose. One problem is the mineral acid-containing aqueous mediums which have been used as the catalyst. Higher hydrogen ion concentration promotes the first order mechanism for furfural destruction. Higher concentration of furfural is another setback in its formation. It has been reported that at fixed acid concentration and temperature, the rate of the destruction of furfural is directly proportional to the concentration of furfural. Because of these reasons, furfural is easily decomposed and polymerized in the conditions necessary for its formation.

What is needed is a new process for producing furfural from xylose.

BRIEF SUMMARY OF THE INVENTION

Disclosed herein are methods, compositions, processes and apparatus for producing furfural from xylose and/or xylose oligosaccharides using sub-critical or near-critical water, optionally in combination with supercritical $CO_2$.

A method of dehydrating xylose to form furfural includes contacting xylose or xylose oligosaccharides (XOS) with subcritical water or a processing fluid comprising water and carbon dioxide in which the temperature and pressure of the processing fluid are above the critical point for carbon dioxide but at least one of the temperature and pressure is below the critical point for water. A process for producing furfural from xylose may include: (a) mixing xylose/XOS with sub-critical or near-critical water to form a mixture at a first temperature and a first pressure; (b) maintaining the mixture at the first temperature and the first pressure for a first time period; and (c) rapidly cooling the mixture to a second temperature and a second pressure, wherein furfural is produced by the process. In another instance, a process for producing furfural from xylose includes: (a) mixing xylose/XOS, $CO_2$, and sub-critical or near-critical water to form a mixture at a first temperature and a first pressure, wherein at the first temperature and the first pressure the mixture is present as a two-phase system comprising an aqueous phase and a $CO_2$-rich phase; (b) maintaining the mixture at the first temperature and the first pressure for a first time period; (c) rapidly cooling the mixture to a second temperature and a second pressure; (d) separating the $CO_2$-rich phase from the aqueous phase; and (e) cooling the $CO_2$-rich phase to a third temperature and a third pressure, wherein furfural is produced by the process.

Also disclosed is a system for dehydrating xylose or hydrolyzing xylose/XOS to form furfural, comprising: a reactor configured for contacting xylose/XOS with a reactive fluid at a temperature and pressure above the critical point of carbon dioxide but at least one of the temperature and pressure of the fluid is beneath the critical temperature and pressure for water; a heating device configured for heating the reactive fluid to the desired temperature; a back-pressure regulator located downstream of the reactor for maintaining the desired pressure; and a heat exchanger configured for cooling the reaction and located downstream of the reactor. In some embodiments, the system further comprises a condenser device configured for condensing at least a portion of the volatile product in the reaction mixture.

Also provided is a composition as described herein, including reaction intermediates as described, or a product produced by any of the processes as described herein or a portion of the processes described, such as xylose in sub-critical water and xylose in a fluid containing water and carbon dioxide in which the fluid has a temperature and pressure above a critical point of carbon dioxide but at least one of the temperature and pressure of the fluid is beneath the critical temperature and pressure for water.

Also provided is a system for producing any of the compositions described herein, or for performing any of the methods or a portion of a method as described herein.

DETAILED DESCRIPTION OF THE INVENTION

Figure 1:
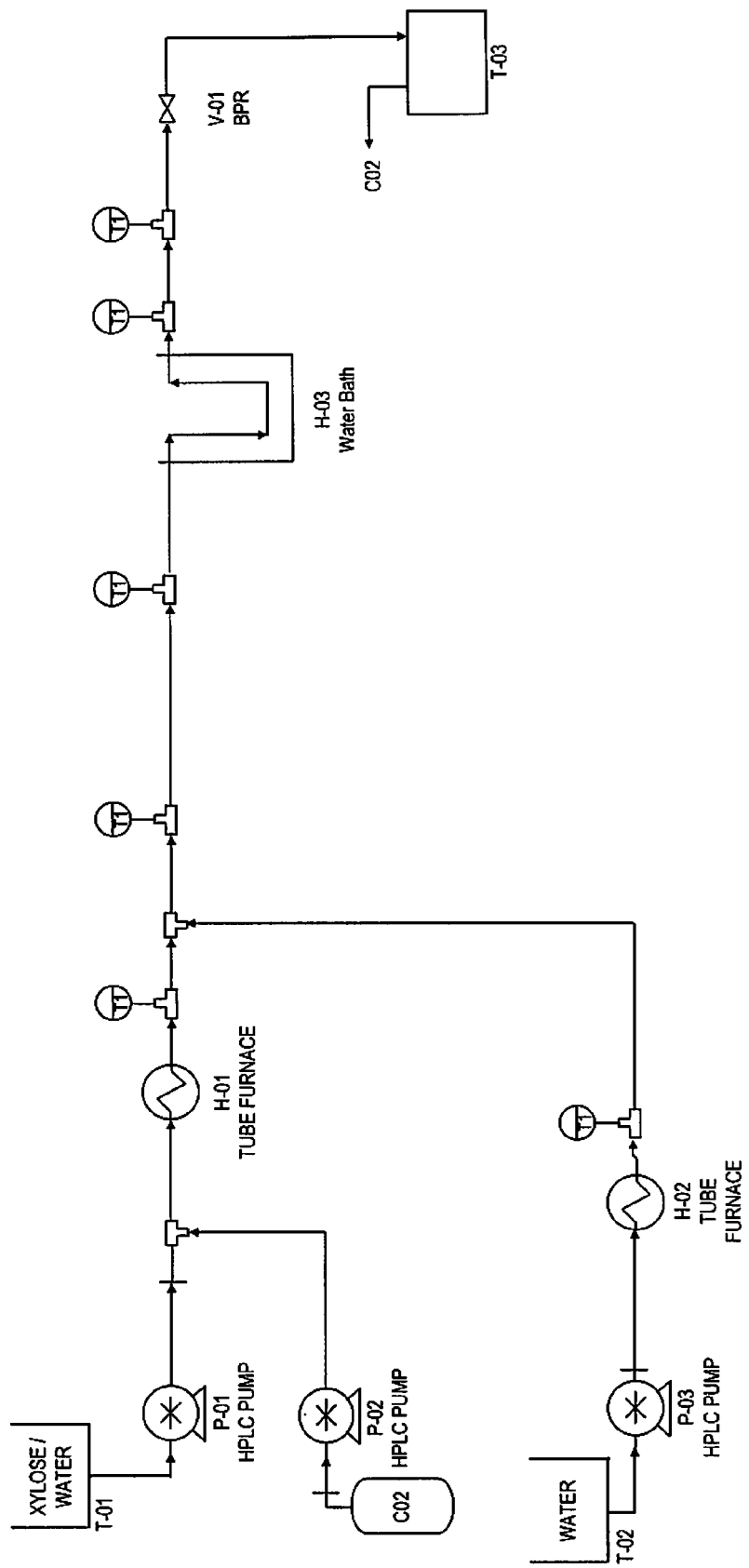
FIG. 1 is a schematic of an exemplary reactor apparatus.

The invention provides a process for producing furfural from xylose, using sub-critical or near-critical water, optionally in combination with supercritical $CO_2$. The methods described herein may provide an economical system for producing furfural from xylose in good yield and selectivity.

A supercritical fluid is a fluid at a temperature above its critical temperature and a pressure above its critical pressure. A supercritical fluid exists at or above its "critical point", the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation. Typical near-critical and supercritical aqueous phases have temperatures in the range from about 250° C. to about 500° C. (or higher) and pressures greater than about 200 bar. The critical temperature for pure water is 374.2° C., and its critical pressure is 221 bar. Carbon dioxide has a critical point of 31° C. and 72.9 atmospheres (about 1072 psig).

Near-critical water has a temperature of about 300° C. to about 374.2° C. Sub-critical water has a temperature of about 100° C. to about 300° C.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of subcritical water and supercritical carbon dioxide" indicates a mixture of water and carbon dioxide at a temperature of about 100° C. to about 300° C.

Briefly, xylose is reacted under hydrothermal conditions (using sub-critical or near-critical water), optionally in the presence of $CO_2$. At sub- and near-supercritical water conditions, xylose undergoes dehydration and loses three water molecules to become furfural:

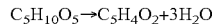

$$C_5H_{10}O_5 \rightarrow C_5H_4O_2 + 3H_2O$$

Xylose oligosaccharides (XOS), which may be obtained from fractionation of biomass together with xylose, breaks down to xylose monomers under the conditions for xylose dehydration described herein and the xylose monomers undergoes dehydration under such conditions. Therefore, any and every embodiments of the hydrothermal processes or any variations thereof described herein for xylose apply to xylose oligosaccharides or a mixture of xylose and xylose oligosaccharides, as if the process is separately described for xylose oligosaccharides or a mixture of xylose and xylose oligosaccharides.

Addition of $CO_2$ to the reaction may facilitate the reaction, and may improve both the yield and the selectivity of furfural. Without wishing to be bound by theory, it is hypothesized that $CO_2$ acts as a catalytic agent, by mixing with the water and forming carbonic acid, thus creating an acidic condition which may catalyze the reaction. Additionally, when sufficient $CO_2$ is added to the reaction mixture such that a 2-phase system (aqueous phase and a $CO_2$-rich phase) is formed, it is hypothesized that the reaction occurs in the aqueous phase (the reaction zone), as xylose is water soluble and present mostly in the aqueous phase, and the $CO_2$-rich phase extracts the furfural away from the reaction zone, hence decreasing the concentration of furfural in the reaction zone and thus decreasing the destruction of the furfural and/or other side reactions.

The process for producing furfural from xylose may be generally as follows. First, xylose in either dry or aqueous form or XOS, for instance, is mixed with sub-critical or near-critical water, and optionally $CO_2$, to form a mixture of xylose/XOS, sub- or near-critical water, and optionally supercritical $CO_2$ at a first temperature and a first pressure. In some embodiments, the mixture to be reacted comprises supercritical $CO_2$. In some embodiments, the mixture to be reacted does not comprise $CO_2$. In some embodiments, the mixture to be reacted does not comprise a mineral acid. In some embodiments, the mixture to be reacted does not comprise hydrochloric, phosphoric, or sulfuric acids. The mixture is kept at the first temperature and the first pressure for a time period for reaction (e.g. the residence time in a reactor or a longer or shorter time, depending on reactor configuration and conditions downstream from the reactor), during which time the xylose reacts to form furfural. Once the desired conversion of xylose to furfural is achieved, the reacted mixture is cooled rapidly to a lower temperature and pressure to quench the reaction.

The xylose/XOS used in the reaction may be from, for example, a commercial source or may be produced by fractionation of a biomass such as a lingo-cellulose biomass (e.g. bagasse, wheat straw, corn stover, and the like). In one embodiment, the xylose and XOS is obtained from a biomass fractionation process according to the methods described in U.S. Provisional Patent Application No. 61/081,346 filed Jul. 16, 2008, the disclosure of which is herein incorporated by reference in its entirety. The xylose solution may contain, for example, about 3 wt % to about 25 wt % xylose, about 3 wt % to about 15 wt % xylose, about 5 wt % to about 15 wt % xylose. In some embodiments, the xylose solution is about 12 wt % xylose. In some embodiments, the xylose solution is about 10 wt % xylose.

In general, the first temperature (the temperature at which dehydration occurs) may be about 200° C. to about 374° C. In various embodiments, the first temperature may be, for example, about 200° C. to about 330° C., about 250° C. to about 374° C., about 250° C. to about 330° C., about 270° C. to about 350° C., about 270° C. to about 330° C., about 270° C. to about 300° C., about 275° C. or about 300° C., about 280° C. to about 300° C., about 280° C. to about 350° C., about 300° C. In some embodiments, the water is near-critical water. In some embodiments, the water is sub-critical water. The first temperature may be adjusted by changing the temperature of the sub-critical or near-critical water and/or by changing the ratio of the aqueous xylose solution to the sub-critical or near-critical water (e.g. by changing the flow rates).

The first pressure may be, for example, about 100 bar to about 350 bar. In some embodiments, the first pressure is about 180 bar to about 320 bar. In some embodiments, the first pressure is about 100 bar to about 220 bar. In some embodiments, the first pressure is about 180 bar to about 220 bar. In some embodiments, the first pressure is above about 225 bar. In some embodiments, the first pressure is about 225 bar.

The temperature and/or pressure at which dehydration occurs may be above the critical point for $CO_2$ but below the critical point for water. Temperatures and pressures may be selected from those discussed above to dehydrate xylose.

The reaction time period may be, for example, about 0.5 to about 180 s. In some embodiments, the reaction time period is about 5 s to about 120 s. In some embodiments, the reaction time period is about 60 s to about 120 s. In some embodiments, the reaction time period is about 3 s to about 30 s. In some embodiments, the reaction time period is about 30 s to about 60 s. In some embodiments, the reaction time period is about 0.5 s to about 35 s. In some embodiments, the reaction time period is about 0.5 s to about 5 s. In some embodiments, the reaction time period is about 2 s to about 5 s. In some embodiments, the reaction time period is about 3 s to about 5 s. In some embodiments, the reaction time period is about 3 s to about 4 s.

The reaction is quenched by rapid cooling (e.g. less than about 1 sec) of the mixture to a lower temperature and pressure. Various methods of rapid cooling may be used, for example, by adding a coolant (e.g. cooled fluid (e.g. cooled water or other appropriate cooled fluid), ice, or other appropriate coolant), by quenching in a heat exchanger with cold fluid indirectly, by immersing the reaction vessel in a cooled bath, by rapid expansion of the reactant mixture (e.g. by expansion through a nozzle), etc. In some embodiments, the cooled fluid is cooled water. In some embodiments, the cooled fluid may have a temperature of, for example, about $-30°$ C. to about $60°$ C., for example about $25°$ C. The lowered temperature may be, for example, about $-10°$ C. to about $60°$ C., for example, about $20°$ C. to about $60°$ C. The lowered pressure may be, for example, about 1 bar to about 75 bar, for example, about 1 atm.

The furfural may be recovered and purified from the reaction product mixture by conventional methods known in the art. For example, the furfural may be recovered from the reaction product mixture by removing the water from the mixture (e.g. by evaporation, distillation, pervaporation, adsorption, extraction of $CO_2$, etc.) to cause precipitation of furfural. Generally, furfural will start to precipitate out of an aqueous furfural solution when the furfural concentration reaches about 5 wt % to about 15 wt %. The furfural product may be purified using conventional methods, e.g. adsorption, chromatography, ion exchange chromatography, etc. The furfural product may be analyzed using conventional methods, e.g. HPLC, GC, etc.

In some embodiments, $CO_2$ is added to the mixture of sub- or near-critical water and xylose/XOS. The $CO_2$ may be added to aqueous xylose solution, and if desired, aqueous xylose solution can be mixed with additional water at subcritical or near-critical conditions. The $CO_2$ may be added to the sub- or near-critical water prior to mixing with xylose/XOS. The $CO_2$ and the sub- or near-critical water may be separately added to xylose/XOS. In some embodiments, the $CO_2$ concentration is low enough that the mixture is a single phase system at the first temperature and first pressure. In some embodiments, the $CO_2$ concentration is such that the mixture is a two-phase system at the first temperature and first pressure, comprising an aqueous phase and a $CO_2$-rich phase. For example, at 4 mol % $CO_2$, the mixture is present as a single phase. At about 40 mol % $CO_2$, the mixture separates into two phases: a $CO_2$-rich phase and an aqueous phase. In various embodiments, the mixture may comprise, for example, about 1 mol % to about 50 mol % $CO_2$, about 4 mol % to about 40 mol % $CO_2$, about 10 mol % to about 40 mol % $CO_2$, about 20 mol % to about 40 mol % $CO_2$, about 30 mol % to about 40 mol % $CO_2$.

In some embodiments, when the $CO_2$ concentration is sufficiently high such that the mixture is a two-phase system at the first temperature and first pressure, after the mixture has reacted at the first temperature and the first pressure for the reaction time period, the reacted mixture may optionally be rapidly cooled to a temperature and pressure at which the water is no longer sub- or near-critical, but wherein the $CO_2$ may optionally be supercritical. For example, the temperature may be rapidly reduced to about $31°$ C. to about $80°$ C., for example about $31°$ C. to about $60°$ C., and the pressure, for example, to about 70 bar to about 120 bar, for example, to about 70 bar to about 80 bar. This process aids in preventing furfural from degrading or reacting further. At this point, the $CO_2$-rich phase (which may comprise co-extracted water) may be separated from the aqueous phase using standards techniques. For example, the $CO_2$-rich phase may be separated from the aqueous phase by refluxing to remove the co-extracted water, which also concentrates the furfural fraction. The flow rate of $CO_2$ may be adjusted to optimize the furfural extraction and vary the reflux ratio to give high furfural yields in the product stream. After separation, the $CO_2$-rich phase may be further cooled and depressurized, for example, to about $-10°$ C. to about $70°$ C., about $20°$ C. to about $70°$ C., for example, about $20°$ C. to about $35°$ C., and for example, to about 1 bar to about 40 bar, for example, to about 1 atm. After furthering cooling and depressurization, the furfural may be separated from the $CO_2$ by conventional techniques.

The process may be a batch process, a semi-batch process, a semi-continuous, or a continuous process, and may utilize conventional chemical reactor technology. In some embodiments, the process is a batch process. In some embodiments, the process is a semi-batch or semi-continuous process. In some embodiments, the process is a batch process. In some embodiments, the process is a continuous process.

In some embodiments, the yield of furfural production increases with increasing xylose conversion. In some embodiments, the selectivity of furfural production increases with increasing xylose conversion. In various embodiments, the yield of furfural production increases with increasing xylose conversion, wherein the xylose conversion level is at least about 50%, at least about 60%, at least about 70%, at least about 80%, at least about 90%. In various embodiments, the selectivity of furfural production increases with increasing xylose conversion, wherein the xylose conversion level is at least about 50%, at least about 60%, at least about 70%, at least about 80%, at least about 90%. Xylose conversion is measured by the amount of xylose and XOS consumed. The yield of furfural is measured by conventional methods, e.g. HPLC analysis, GC analysis, etc. The selectivity is measured by the yield of furfural produced relative to the total theoretical yield based on total xylose consumption. In some embodiments, the addition of $CO_2$ enhances production of furfural.

Also disclosed is a system for dehydrating xylose or hydrolyzing xylose/XOS to form furfural, comprising a reactor configured for contacting cellulose with a reactive fluid at a temperature and pressure above the critical point of carbon dioxide but at least one of the temperature and pressure of the fluid is beneath the critical temperature and pressure for water. In some embodiments, the reactor is configured for contacting xylose/XOS with a reactive fluid at a temperature of up to about $250°$ C., about $300°$ C., about $350°$ C., about $375°$ C. or about $400°$ C. and a pressure of up to about 100 bar, about 150 bar, about 200 bar, about 250 bar, about 300 bar, or about 350 bar. In some embodiments, the system further comprises a heating device configured for heating the reactive fluid to the desired temperature and a back-pressure regulator located downstream of the reactor for maintaining the desired pressure. In some embodiments, the system may further comprise a heat exchanger configured for cooling a reaction located downstream of the reactor. In some embodiments, the system may further comprise a condenser device configured for condensing and collecting a volatile product (e.g. furfural) in a reaction mixture, such as a cold trap cooled with e.g. cold water, ice or dry ice.

In some embodiments, the system for dehydrating xylose or hydrolyzing xylose/XOS to form furfural, may further comprise additional apparatus such as vessels for holding the fluids or slurry, devices for monitoring the temperatures and pressures, and modules for date collection and safety controls. In some embodiments, a system may further comprise a composition comprising xylose and/or furfural, water, and optionally $CO_2$.

Also provided are various compositions such as xylose in sub-critical water and xylose in a fluid containing water and carbon dioxide in which the fluid has a temperature and pressure above a critical point of carbon dioxide but at least one of the temperature and pressure of the fluid is beneath the critical temperature and pressure for water. In some embodiments, the composition comprises xylose/XOS and sub-critical water, e.g. xylose/XOS and water at about 100° C. to about 300° C. In some embodiments, the composition comprises xylose/XOS and water at a pressure of about 100 to about 350 bars. In some embodiments, the composition comprises xylose/XOS and sub-critical water at about 100° C. to about 300° C. and about 100 to about 350 bars. In some embodiments, the composition comprises about 3 wt % to about 25 wt %, about 3 wt % to about 15 wt %, about 5 wt % to about 15 wt % xylose/XOS. In some embodiments, the composition comprises about 12 wt % xylose/XOS. In some embodiments, the composition comprises about 10 wt % xylose/XOS.

In some embodiments, provided is a composition comprising xylose/XOS, supercritical $CO_2$ and sub-critical water. In some embodiments, the composition comprises xylose/XOS, $CO_2$ and water at about 100° C. to about 300° C. In some embodiments, the composition comprises xylose/XOS, $CO_2$ and water at about 100° C. to about 300° C. and about 100 to about 350 bars. In some embodiments, the composition comprises about 3 wt % to about 25 wt %, about 3 wt % to about 15 wt %, about 5 wt % to about 15 wt % xylose/XOS. In some embodiments, the $CO_2$ concentration is low enough that the composition is a in a single phase. In some embodiments, the $CO_2$ concentration is such that the composition is in a two-phase system, comprising an aqueous phase and a $CO_2$-rich phase. For example, at 4 mol % $CO_2$, the composition may be present as a single phase. At about 40 mol % $CO_2$, the composition separates into two phases: a $CO_2$-rich phase and an aqueous phase. In various embodiments, the composition may comprise, for example, about 1 mol % to about 50 mol % $CO_2$, about 4 mol % to about 40 mol % $CO_2$, about 10 mol % to about 40 mol % $CO_2$, about 20 mol % to about 40 mol % $CO_2$, about 30 mol % to about 40 mol % $CO_2$.

The practice of this invention can be further understood by reference to the following examples, which are provided by way of illustration and are not intended to be limiting. Although exemplified by the conditions (e.g. temperature, pressure, time, etc.) and examples provided herein, the invention is not limited by the conditions and examples provided herein. The invention contemplates all suitable conditions that can be identified by routine optimization in light of the disclosures provided herein.

EXAMPLES

Example 1

Solvo-Thermal Conversion of Xylose to Furfural

Xylose used in Examples 1-3 was purchased from Aldrich. Water was purified using a Barnstead NANOpure Infinity® purification system. $CO_2$ was acquired from Airgas.

FIG. 1 illustrates the use of a continuous reaction process. Xylose and water were added to tank T01 and mixed well. The gas cylinder contained liquid carbon dioxide. The xylose, water and carbon dioxide from two tanks T-01 and T-02 were pumped by High Pressure Pumps (P 01 & P 02). In this setup, the aqueous xylose solution (T01) and sub-critical or near-critical water (T02) were contacted by injection into the reactor. There was continuous monitoring of reaction temperature, pressure, and time. Reaction occurs at predetermined pressure and temperature conditions for desired residence time. After exiting, the stream was passed through a cooled water bath (H 03) to bring it to a necessary cooling temperature. Furfural was separated from the mixture using super-critical carbon dioxide extraction or other techniques, and collected in tank (T03) where unconverted xylose/water mixture was diverted for recycling back into the reaction process.

The above setup was used to study hydrothermal conversion of xylose. Xylose feed solution of 10 wt % in water was prepared. HPLC pumps were used to pump all streams. In reactions with $CO_2$, the $CO_2$ was mixed with the xylose feed stream.

Reaction products samples were filtered (using 0.2 μm syringe membrane filter) and analyzed using GC-MS. HPLC analysis was used to determine unconverted xylose with a Transgenomic® sugars column (maintained at 80° C.) and refractive index detector. The mobile phase was distilled water at a flow rate of 0.5 ml/min. Calibration curves were constructed for the compounds of interest, and concentrations of those species were determined for the various reaction conditions.

Example 2

Xylose Conversion and Furfural Yields

Figure 2:
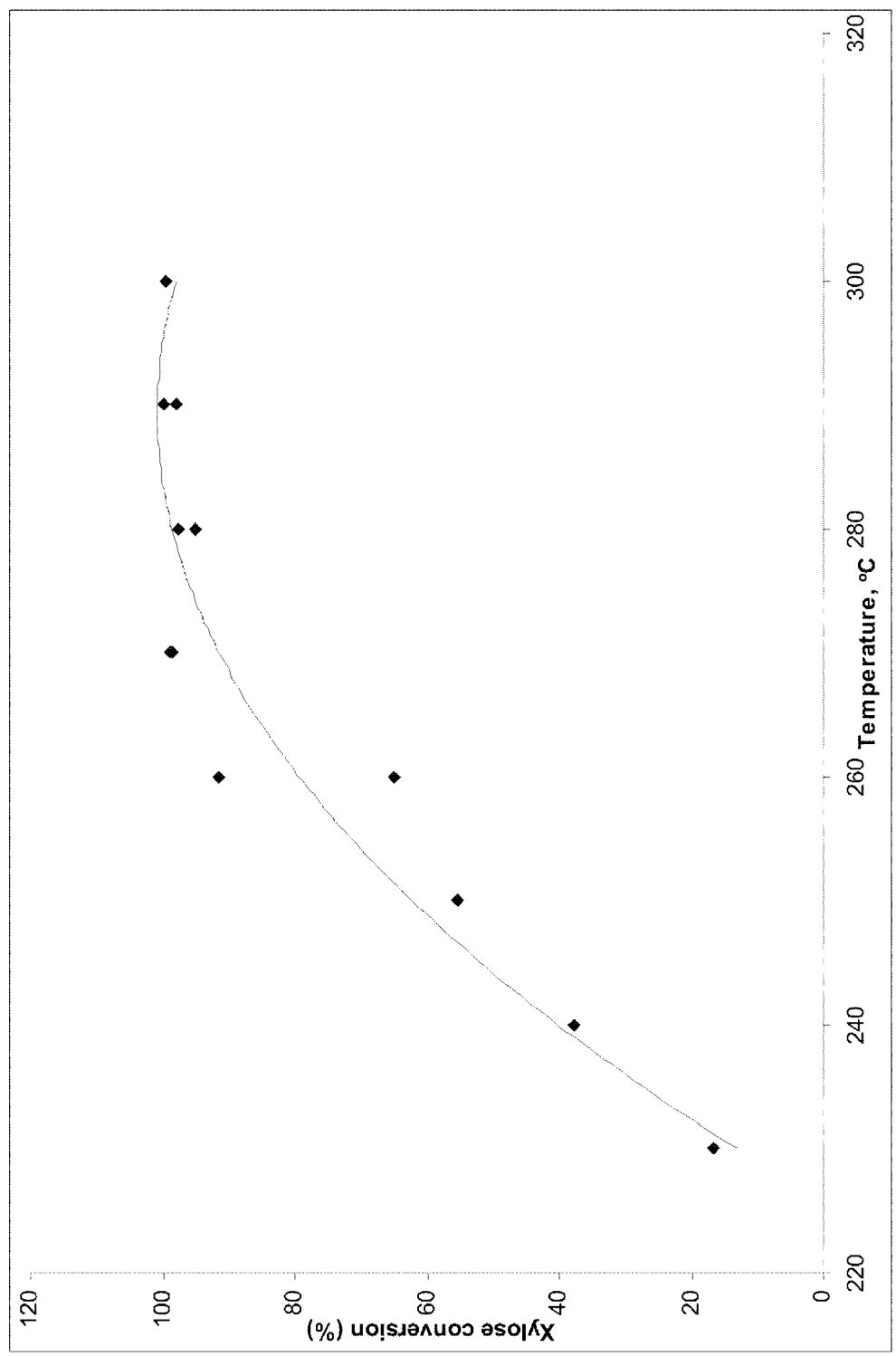
FIG. 2 is a plot of effect of temperature on the conversion of xylose.
Figure 3:
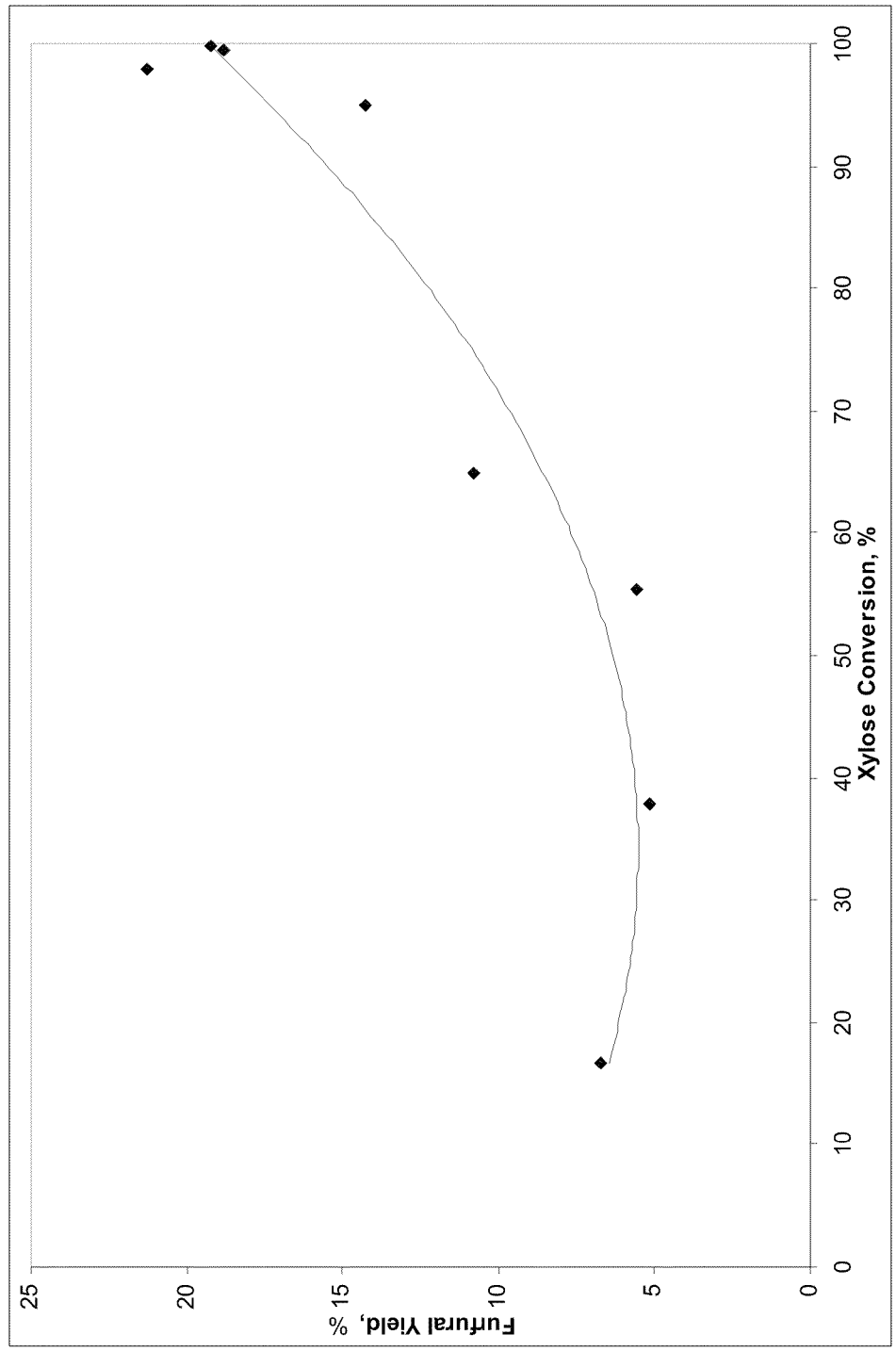
FIG. 3 is a plot showing the relationship between conversion of xylose and the furfural yield.
Figure 4:
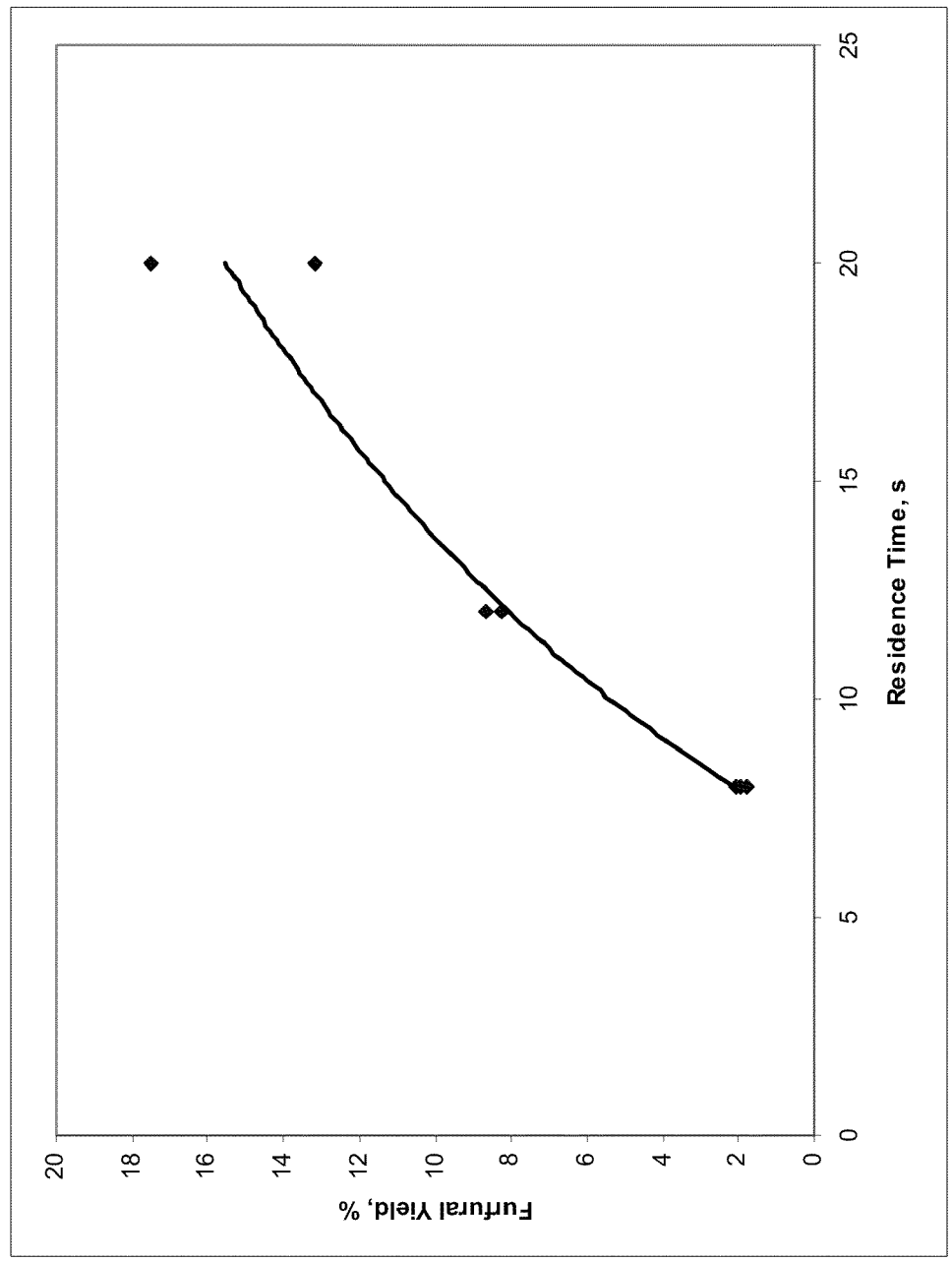
FIG. 4 is a plot of furfural yield at different residence times.
Figure 5:
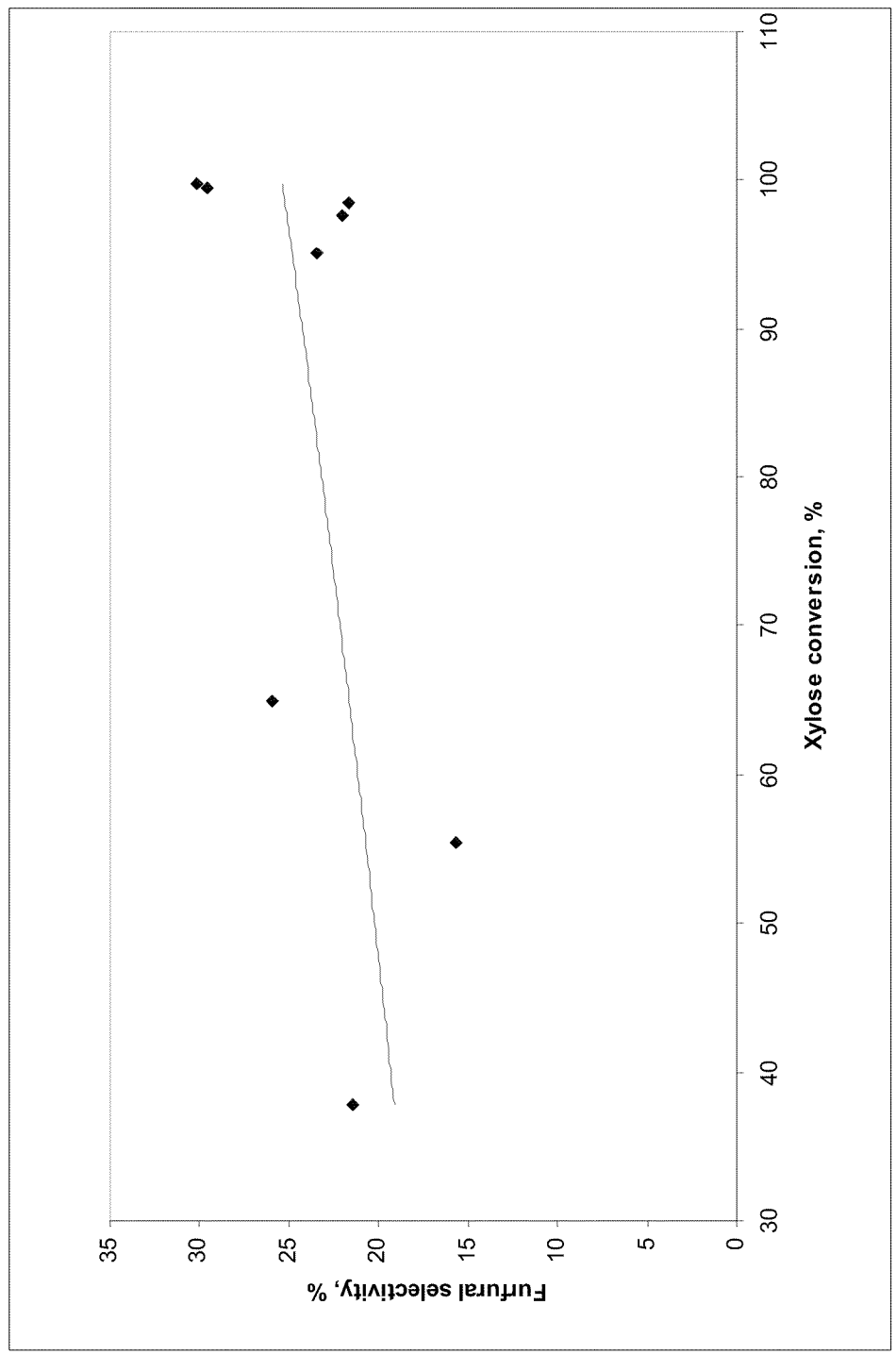
FIG. 5 is a plot of the selectivity toward furfural production versus xylose conversion.
Figure 6:
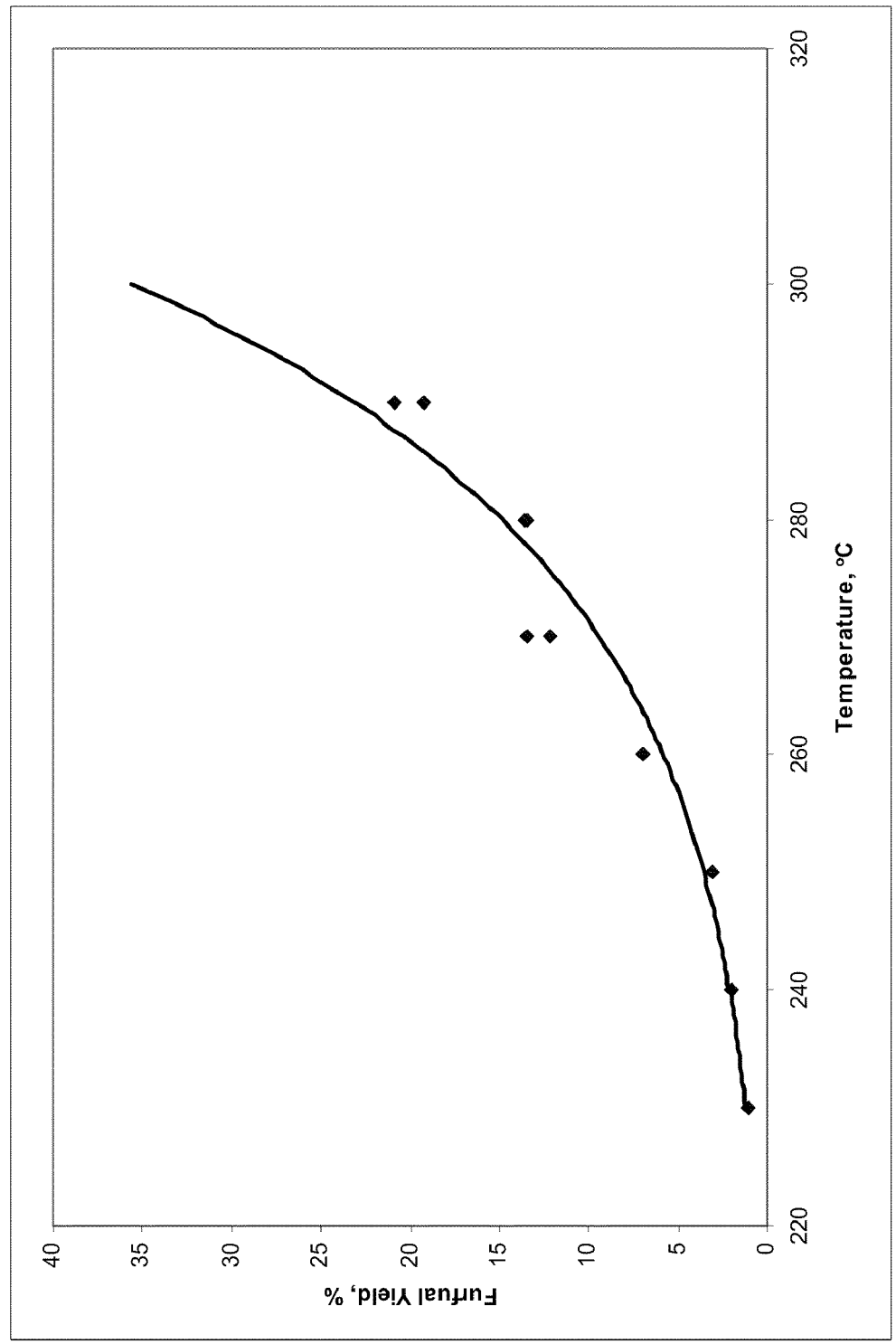
FIG. 6 shows the effect of temperature on the furfural yield (percentage of original xylose).
Figure 7:
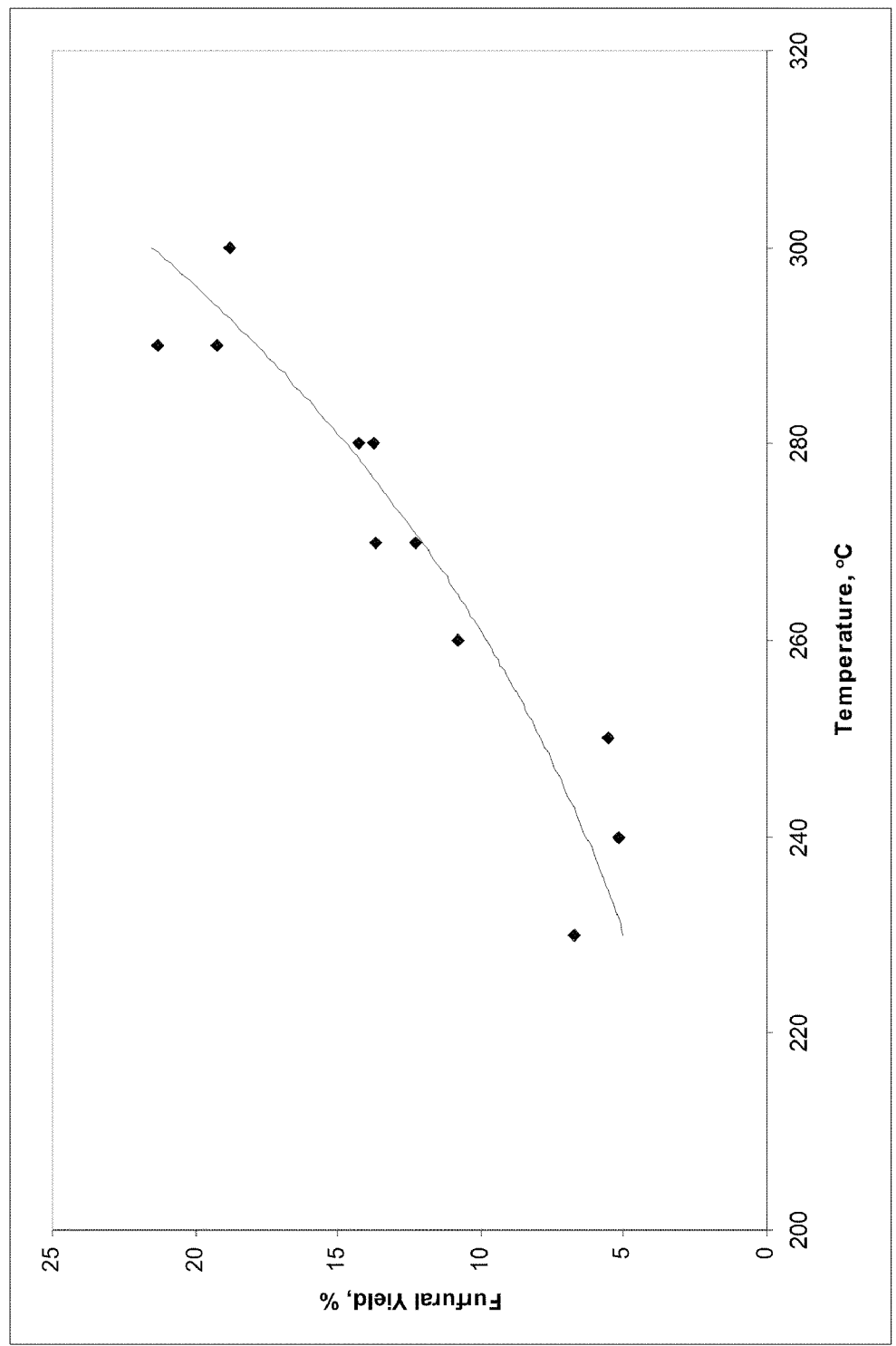
FIG. 7 is a plot of furfural yield (percentage of converted xylose) versus temperature.

FIG. 2 shows xylose conversion in water plotted against temperatures of 230° C. and 300° C., with zero residence time. Xylose conversion increased with the increase in the temperature and attained above 90% conversion at 270° C. Furfural yield also increased with xylose conversion as shown in FIG. 3. Furfural yield increased with increasing residence time from 4 to 20 s which is demonstrated in FIG. 4. The same trend was observed in a plot of the furfural selectivity versus xylose conversion (FIG. 5). The furfural yield also increased with temperature, which is shown as percentage of original xylose in FIG. 6 and percentage of converted xylose in FIG. 7. The yield and selectivity both increased with increasing xylose conversion, even as the xylose conversion neared 100% (FIGS. 3 and 5).

Example 3

Xylose Conversion with $CO_2$

Figure 8:
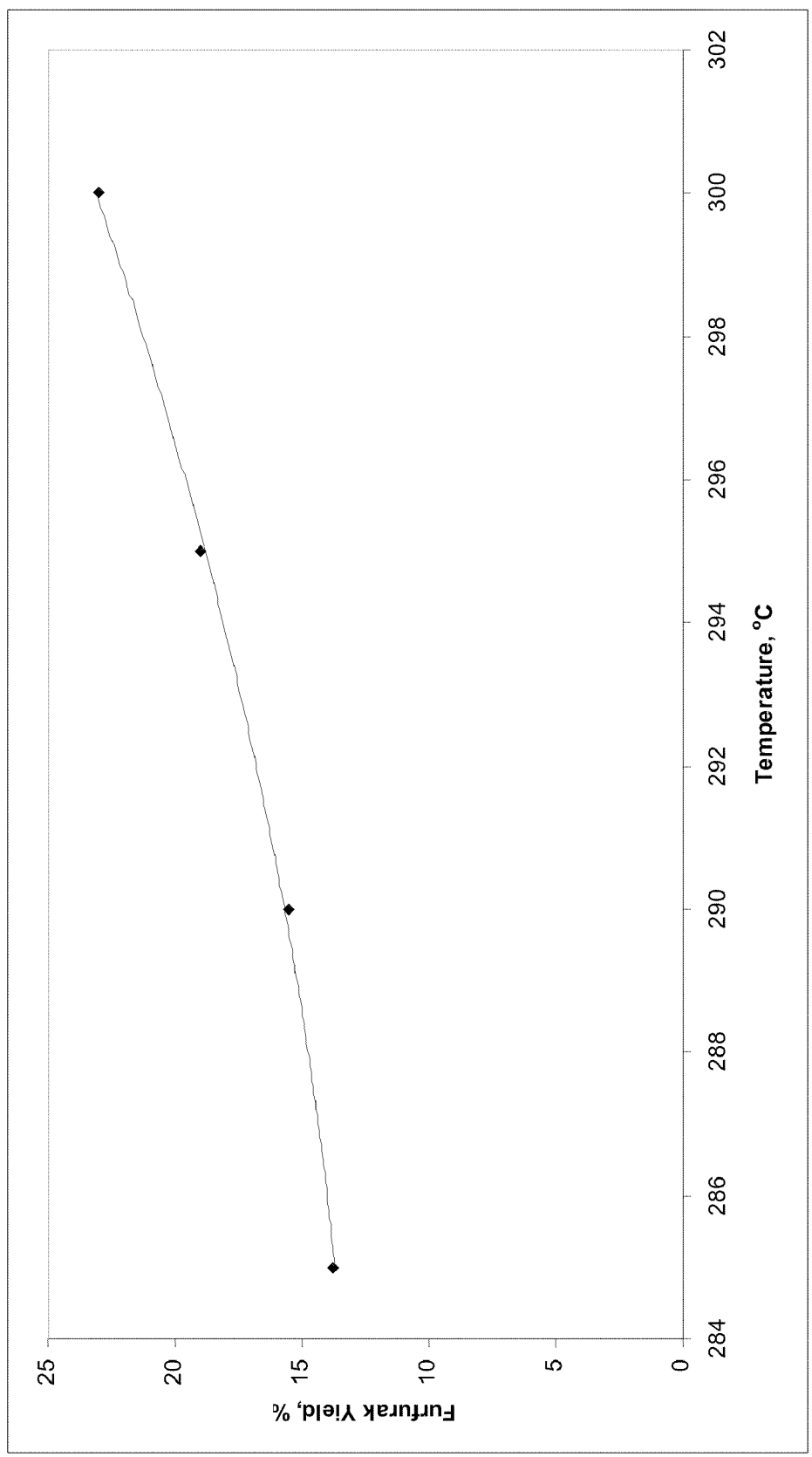
FIG. 8 is a plot of the furfural yield produced with carbon dioxide versus temperature.
Figure 9:
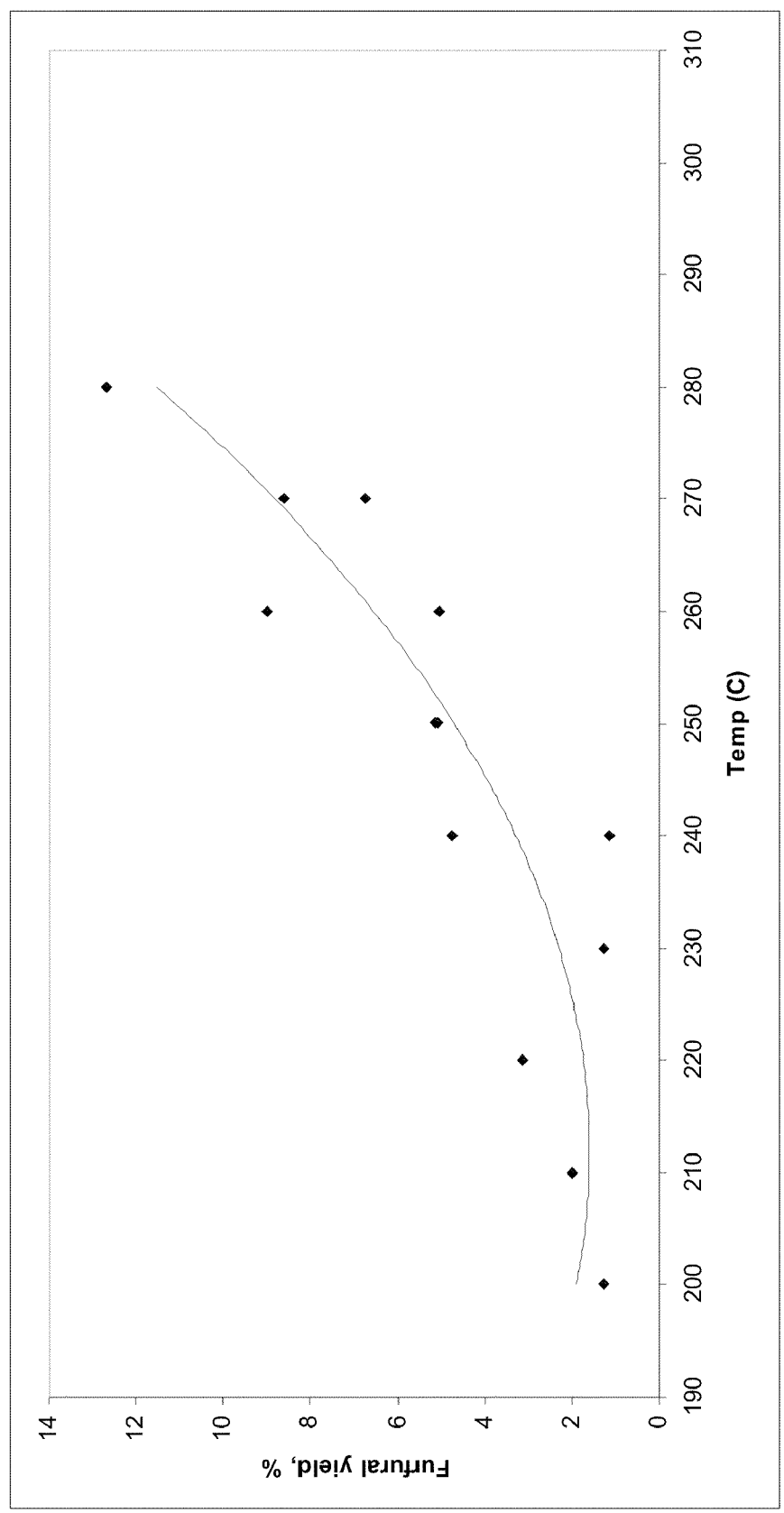
FIG. 9 is a plot of furfural yield produced without carbon dioxide versus temperature at zero residence time in a continuous system.

FIG. 8 shows data for xylose conversion with $CO_2$ addition. Addition of carbon dioxide increased furfural yield as indicated in FIG. 8 and compared to FIG. 9. Effect of carbon dioxide addition on furfural yield was also higher at higher temperatures. Furfural yield and selectivity increased with the addition of $CO_2$, indicating an enhancement of the desired reactions. The effect of $CO_2$ was investigated further in additional experiments with enough and excess $CO_2$. The results of these experiments revealed no significant differences between the two conditions for a given temperature. Furfural yield and selectivity both increased with residence time, with the higher $CO_2$ concentration yielding sharper increases.

Example 4

Conversion of Xylose from Biomass Fractionation with $CO_2$

Figure 10:
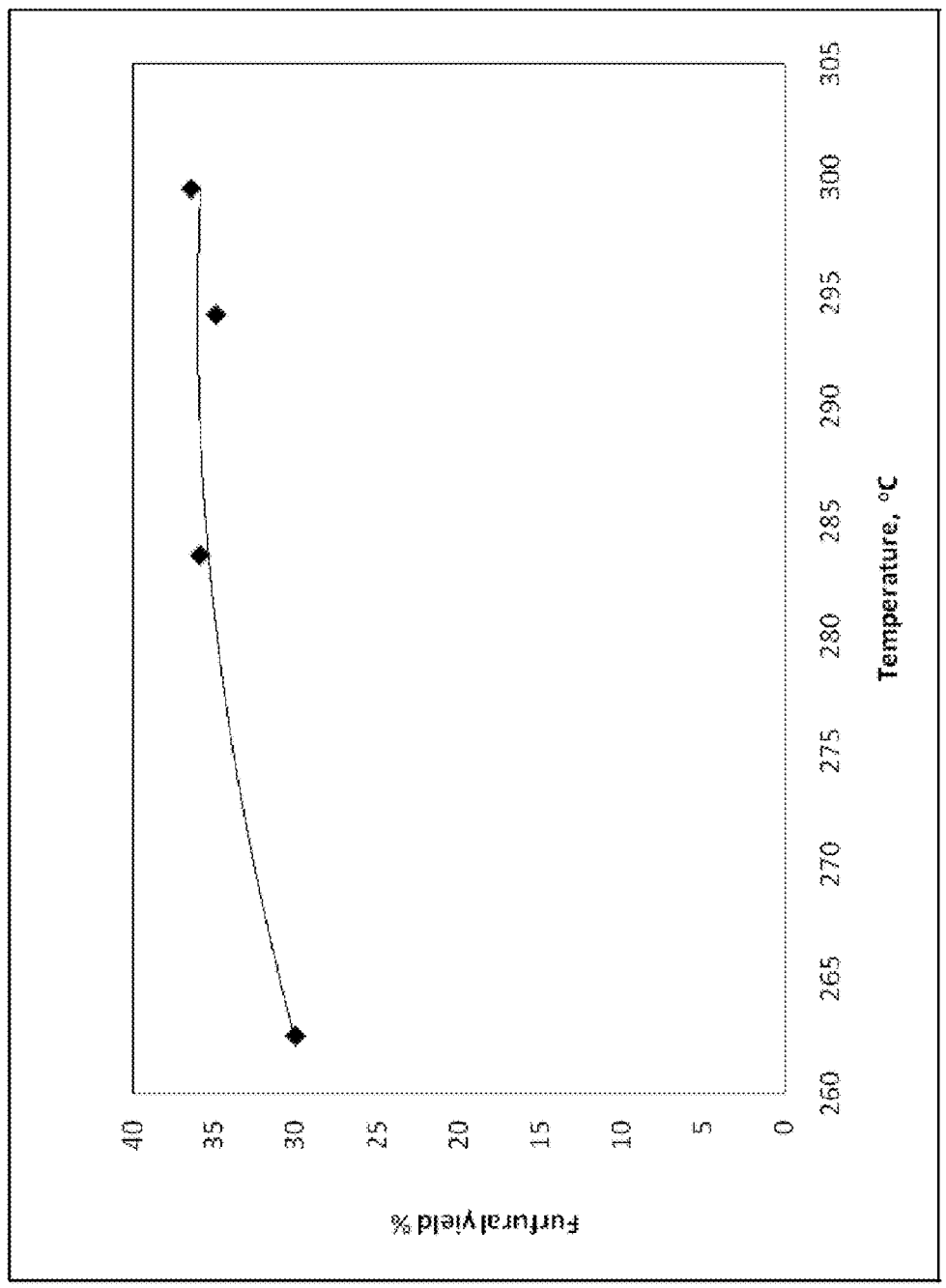
FIG. 10 is a plot of furfural yield from hydrolysis of xylose liquor from fractionation of lignocellulosic biomass, produced with carbon dioxide.

A xylose liquor from fractionation of lignocellulosic biomass as described in U.S. Provisional Patent Application No. 61/081,346 was converted to furfural with carbon dioxide. A correlation of the yields of furfural produced with the reaction temperature is shown in FIG. 10.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

All patents, patent applications, documents, and articles cited herein are incorporated by reference in their entireties.

What is claimed is:

1. A process for producing furfural from xylose comprising:
   (a) mixing xylose/XOS with sub-critical or near-critical water to form a mixture
   at a first temperature and a first pressure;
       wherein the first temperature is about 200° C. to about 374° C.; and
       wherein the first pressure is about 100 bar to about 350 bar;
   (b) maintaining the mixture at the first temperature and the first pressure for a first time period;
       wherein the first time period is about 0.5 s to about 180 s; and
   (c) rapidly cooling the mixture to a second temperature and a second pressure; wherein furfural is produced by the process;
       wherein the second temperature is about −30° C. to about 60° C.; and
       wherein the second pressure is about 1 atm to about 75 atm.

2. The process of claim 1, wherein the furfural is recovered by removing the water from the mixture to cause precipitation of furfural.

3. The process of claim 1, wherein the aqueous xylose solution is mixed with the sub-critical or near-critical water in a mixing ratio, and the first temperature is adjusted by changing the mixing ratio and/or by changing the temperature of the sub-critical or near-critical water.

4. The process of claim 1, wherein the mixture is cooled by adding a coolant.

5. The process of claim 1, wherein the xylose is converted at a conversion level and furfural is produced in a yield and a selectivity, wherein the yield and the selectivity of furfural production increase with increasing xylose conversion levels.

6. The process of claim 5, wherein the xylose/XOS conversion level is at least about 60%.

7. The process of claim 1, wherein the mixture further comprises $CO_2$.

8. The process of claim 7, wherein at the first temperature and the first pressure the mixture is present as a two-phase system comprising an aqueous phase and a $CO_2$-rich phase.

9. The process of claim 7, wherein the mixture comprises about 1 mol % to about 50 mol % $CO_2$.

10. The process of claim 7, wherein the $CO_2$ is added to the aqueous xylose solution prior to mixing the aqueous xylose solution with the sub-critical or near-critical water.

11. A process for producing furfural from xylose comprising:
   (a) mixing xylose/XOS, $CO_2$, and sub-critical or near-critical water to form a mixture at a first temperature and a first pressure, wherein at the first temperature and the first pressure the mixture is present as a two-phase system comprising an aqueous phase and a $CO_2$-rich phase;
   (b) maintaining the mixture at the first temperature and the first pressure for a first time period;
       wherein the first temperature is about 200° C. to about 374° C. the first pressure is about 100 bar to about 350 bar and the first time period is about 0.5 s to about 180 s.
   (c) rapidly cooling the mixture to a second temperature and a second pressure;
   (d) separating the $CO_2$-rich phase from the aqueous phase; and
       wherein the second temperature is about 31° C. to about 60° C. and the second pressure is about 70 bar to about 100 bar
   (e) cooling the $CO_2$-rich phase to a third temperature and a third pressure;
       wherein furfural is produced by the process wherein the third temperature is about −10° C. to about 50° C. and the third pressure is about 1 atm to about 70 atm.

12. The process of claim 11, wherein the mixture comprises about 1 mol % to about 50 mol % $CO_2$.

13. The process of claim 1 or 11, wherein the xylose/XOS is added to the process as an aqueous slurry.

* * * * *